United States Patent
Schmaltz

(10) Patent No.: US 7,749,220 B2
(45) Date of Patent: Jul. 6, 2010

(54) PERCUTANEOUS OR SURGICAL RADIOFREQUENCY INTRAVASCULAR THROMBECTOMY CATHETER SYSTEM AND METHOD

(75) Inventor: Dale F. Schmaltz, Fort Collins, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 586 days.

(21) Appl. No.: 11/391,620

(22) Filed: Mar. 28, 2006

(65) Prior Publication Data

US 2006/0224155 A1 Oct. 5, 2006

Related U.S. Application Data

(60) Provisional application No. 60/666,830, filed on Mar. 31, 2005.

(51) Int. Cl.
*A61B 18/14* (2006.01)
(52) U.S. Cl. ........................................................ 606/41
(58) Field of Classification Search ............... 606/7, 606/41–42, 49–50, 159, 200
See application file for complete search history.

(56) References Cited

U.S. PATENT DOCUMENTS

| | | | |
|---|---|---|---|
| 5,178,620 A * | 1/1993 | Eggers et al. | 606/41 |
| 5,419,767 A * | 5/1995 | Eggers et al. | 604/114 |
| 5,972,019 A * | 10/1999 | Engelson et al. | 606/200 |
| 6,068,645 A | 5/2000 | Tu | |
| 6,102,908 A | 8/2000 | Tu et al. | |
| 6,129,739 A | 10/2000 | Khosravi | |
| 6,622,367 B1 * | 9/2003 | Bolduc et al. | 29/447 |
| 2002/0183682 A1 | 12/2002 | Darvish et al. | |
| 2002/0183686 A1 | 12/2002 | Darvish et al. | |
| 2003/0060822 A1 | 3/2003 | Schaer et al. | |
| 2003/0100919 A1 * | 5/2003 | Hopkins et al. | 606/200 |
| 2003/0114747 A1 * | 6/2003 | Smith | 600/420 |
| 2005/0096647 A1 * | 5/2005 | Steinke et al. | 606/41 |

FOREIGN PATENT DOCUMENTS

JP 2001293084 A * 10/2001

OTHER PUBLICATIONS

International Search Report from Application No. EP 06 00 6962 dated Aug. 3, 2007.

* cited by examiner

*Primary Examiner*—Lee S Cohen

(57) ABSTRACT

The present disclosure relates to intravascular thrombectomy systems and methods for ablating a blockage and preventing the introduction of emboli into the blood stream during and after surgery performed to reduce or ablate the blockage in a blood vessel. The system includes a catheter sleeve having electrodes disposed proximate a distal end portion thereof, either at the distal end itself or axially spaced along the length of the catheter sleeve. The system further includes a capture element which is expandable to span the lumen of the vessel. The capture element is deployable downstream of the blockage. The electrodes of the catheter sleeve may be placed on one side of the blockage or on either side of the blockage.

17 Claims, 6 Drawing Sheets

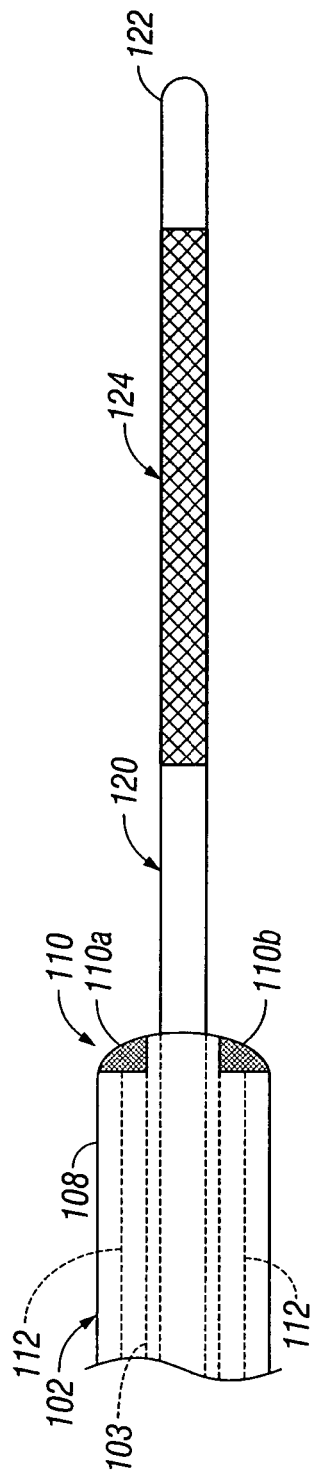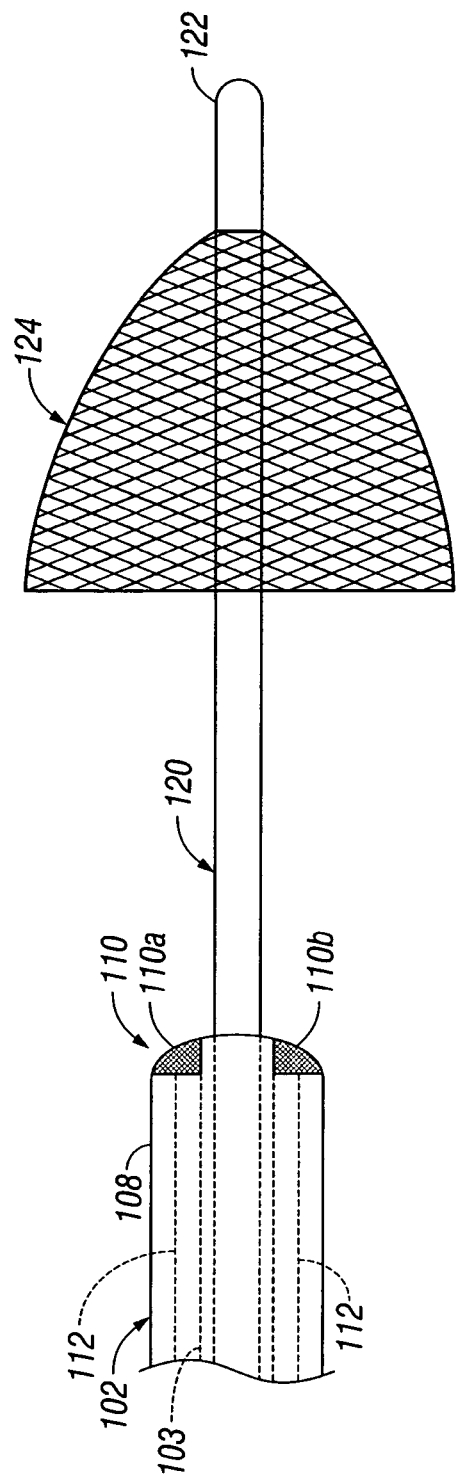

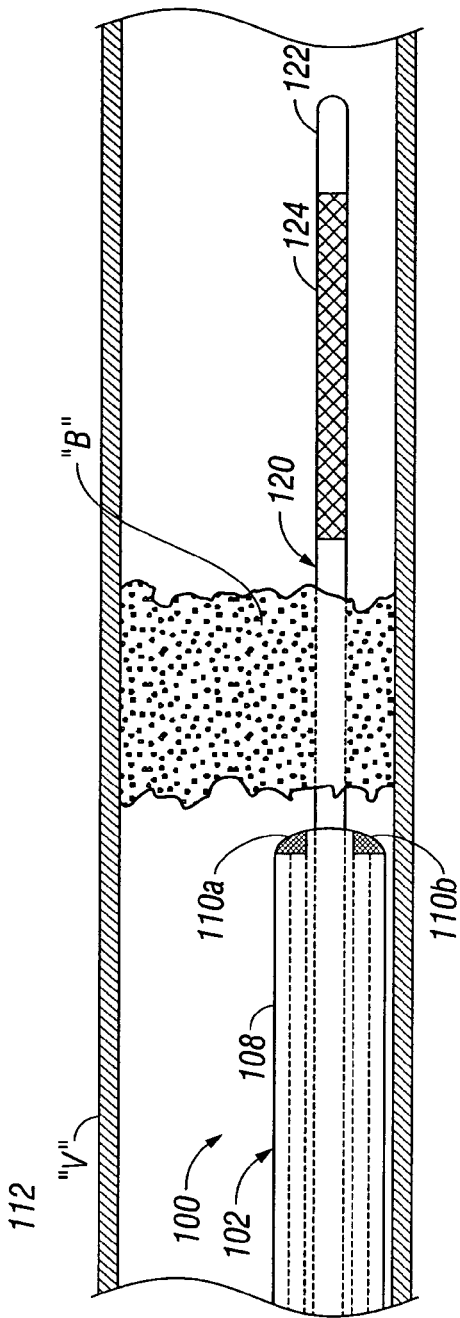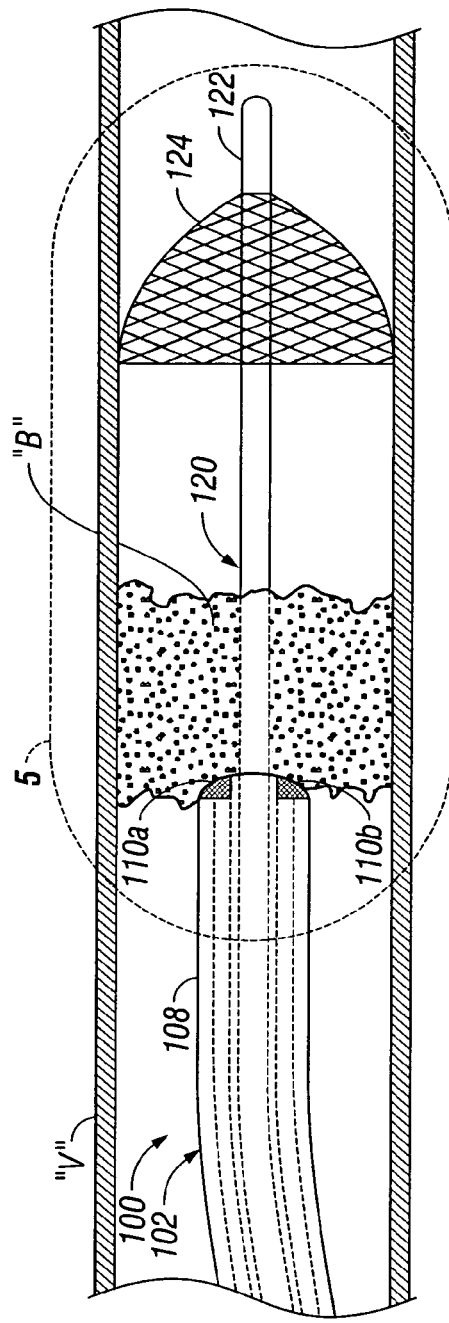

PERCUTANEOUS OR SURGICAL RADIOFREQUENCY INTRAVASCULAR THROMBECTOMY CATHETER SYSTEM AND METHOD

CROSS-REFERENCE TO RELATED APPLICATION

The present application claims the benefit of and priority to U.S. Provisional Application Ser. No. 60/666,830, filed on Mar. 31, 2005, the entire content of which is incorporated herein by reference.

BACKGROUND

1. Technical Field

The present disclosure relates to intravascular thrombectomy systems and methods and, more particularly, to intravascular systems and methods used to ablate a blockage and to prevent the introduction of emboli into the blood stream during and after surgery performed to reduce or ablate the blockage in the blood vessel.

2. Background of Related Art

As is known in the industry, a thrombosis is the formation or presence of a thrombus or blood clot inside a blood vessel or cavity of the heart. An embolus meanwhile is a thrombus or blood clot that moves through the bloodstream until it lodges in a narrowed vessel and blocks circulation.

The narrowing or occluding of blood vessels, such as the walls of an artery, inhibits normal blood flow. Such blockages, whether partial or full, can have serious medical consequences depending upon their location within a patient's vascular system. For example, the narrowing or blocking of the coronary vessels that supply blood to the heart may cause damage to the heart.

Various surgical procedures are currently used to remove or reduce the blockage in the blood vessels. Such procedures include balloon angioplasty, which involves inserting a balloon catheter into the narrowed or occluded area, expanding the balloon in the narrow or occluded area, and if necessary, placing a stent in the now expanded area to keep it open. Another common procedure used is atherectomy where the lesion is cut away and removed from the vessel, or abrasively ground, sending the small particulates downstream. Other endovascular procedures make use of thrombectomy, drug delivery, radiation, stent-grafts, and various diagnostic devices.

On occasion, a large thrombus or a platelet-rich thrombus resists pharmacological therapy. In such instances, restoration of adequate antegrade coronary or peripheral flow necessitates application of a device that is capable of removing the thrombus or blockage, as described above. Present mechanical devices for power thrombectomy include ultrasound sonication, rheolytic thrombectomy, laser transluminal extraction catheterization, aspiration catheterization, and balloon angioplasty.

Ultimately, the clinical strategy is to use any one or a combination of procedures disclosed above to achieve nearly complete vessel patency, improved antegrade flow, and enhanced preservation of myocardial tissue.

However, each of the above described procedures carries with it the risk that some of the treated plaque will be disrupted, resulting in embolic particulates released in the bloodstream. These emboli, if allowed to flow through the vascular system, may cause subsequent infarctions or ischemia in the patient.

Systems have been developed to prevent the emboli from being released into the bloodstream during such procedures. For example, in one system, a balloon may be used to completely occlude the artery distal (i.e., downstream) of the area of blockage to be treated. In another system, a filter may be used to prevent emboli from being released into the bloodstream during surgical intervention.

SUMMARY

The present disclosure relates to intravascular thrombectomy systems and methods.

According to an aspect of the present disclosure, a catheter system for ablating a partial or a complete blockage of a corporal vessel is provided. The catheter system includes a catheter sleeve having a distal end portion; a capture element disposed proximate the distal end portion of the catheter sleeve; and at least a pair of axially spaced apart electrodes supported on the catheter sleeve at a location proximal of the capture element. Each electrode is connectable to a source of electrosurgical energy. The capture element has a first condition wherein the capture element is retracted onto the catheter sleeve and a second condition wherein the capture element at least substantially spans the entire lumen of the vessel. The catheter sleeve may be flexible and may enable pushability and trackability. The catheter sleeve may have a gauge of about 0.060 inches.

The catheter system may include a source of electrosurgical energy electrically connectable to each electrode. The electrosurgical energy source may deliver an effective amount of energy to the electrodes to ablate the blockage.

According to yet another aspect of the present disclosure, a method of ablating a blockage in a corporal vessel is provided. The method includes the steps of providing a catheter system configured and adapted to ablate the blockage. The catheter system includes a catheter sleeve having a distal end portion supporting at least a pair of electrodes thereon, and an electrosurgical energy source connectable to each electrode.

The method further includes the steps of introducing the catheter into the corporal vessel, advancing the catheter sleeve through the corporal vessel to the blockage, positioning a capture element downstream of the blockage, and deploying the capture element to at least substantially span the lumen of the corporal vessel. The method further includes the steps of positioning the catheter sleeve within the corporal vessel such that at least one electrode is positioned in close proximity to the blockage, and activating the electrosurgical energy source to energize the electrodes and ablate the blockage.

The method may further include the step of delivering an effective amount of energy for an effective amount of time to the blockage.

According to one method, the catheter assembly may include a guidewire slidably supported within a lumen of the catheter sleeve. The catheter sleeve may include a pair of electrodes operatively supported at the distal end portion thereof. The guidewire may include a capture element operatively supported on a distal end portion thereof. The capture element may include a first condition wherein the capture element is retracted onto the guidewire and a second condition wherein the capture element at least substantially spans the entire lumen of the vessel.

The method may further include the steps of extending the guidewire distally from the catheter sleeve and through the blockage until the capture element is disposed completely beyond the blockage; and advancing the catheter sleeve through the corporal vessel until the distal end portion thereof is in contact with the blockage.

According to another method, the catheter sleeve may support a capture element proximate a distal end portion thereof. At least a pair of axially spaced apart electrodes is disposed on the catheter sleeve at a location proximal of the capture element.

The method may further include the step of advancing the catheter sleeve through the corporal vessel and through the blockage until the capture element and a distal-most electrode is positioned distal of the blockage.

Each electrode of the catheter system may be electrically independent from one another.

Additional objects and advantages of the disclosure will be set forth in part in the description which follows, and in part will be obvious from the description, or may be learned by practice of the invention. The objects and advantages of the invention will be realized and attained by means of the elements and combinations particularly pointed out in the appended claims.

Both the foregoing general description and the following detailed description are exemplary and exploratory only and are not restrictive of the invention, as claimed.

BRIEF DESCRIPTION OF THE DRAWINGS

The accompanying drawings, which are incorporated in and constitute a part of the specification, illustrate several embodiments of the invention and together with the description, serve to explain the principles of the invention. In the drawings:

FIG. 2 is an enlarged view of the indicated area of detail of FIG. 1, illustrating the thrombectomy catheter system in a first condition;

FIG. 3 is an enlarged view of the indicated area of detail of FIG. 1, illustrating the thrombectomy catheter system in a second condition;

FIGS. 4A-4D illustrate a generalized sequence of steps for use of the thrombectomy catheter system of FIGS. 1-3 for restoration of flow past the occluded site;

DETAILED DESCRIPTION OF EMBODIMENTS

Figure 1:
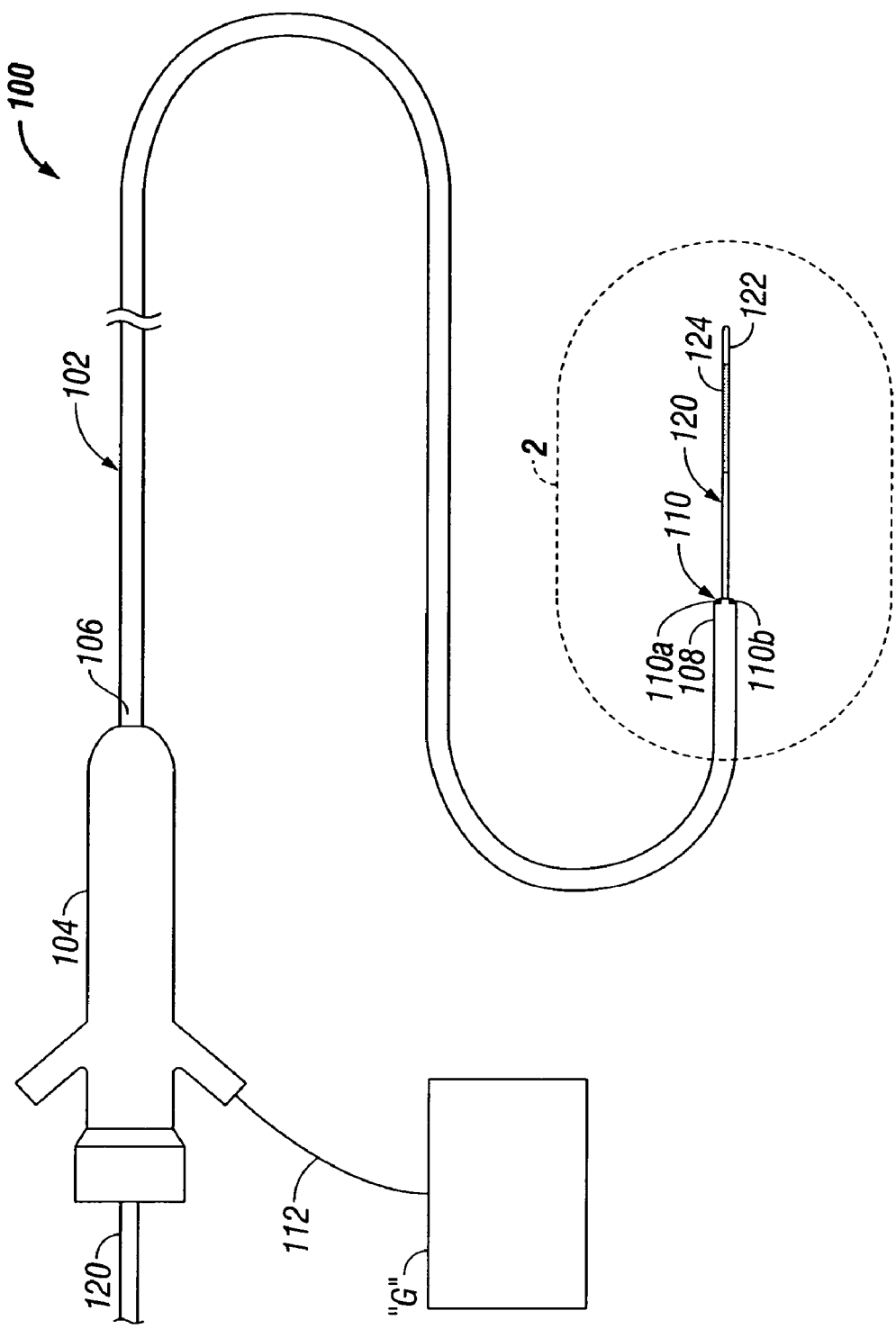
FIG. 1 is schematic illustration of a thrombectomy catheter system according to an embodiment of the present disclosure.

Reference will now be made in detail to the present embodiments of the disclosure, examples of which are illustrated in the accompanying drawings. Wherever possible, identical or similar reference numerals will be used throughout the drawings to refer to similar or like elements.

The present disclosure provides for devices and methods for ablating a blockage and for preventing the introduction of emboli into the blood stream during and after surgery performed to reduce or ablate the blockage in the blood vessel. As used herein, and "occlusion," "blockage," or "stenosis" refers to both complete and partial blockages of the vessel.

Additionally, as used herein, "proximal" refers to that portion of the device or apparatus located closest to the user, and "distal" refers to that portion of the device or apparatus located furthest from the user.

Referring initially to FIGS. 1-3, a thrombectomy catheter system, in accordance with an embodiment of the present disclosure, is generally designated 100. Thrombectomy catheter system 100 includes an elongate catheter sleeve 102 having a substantially tubular configuration. Catheter sleeve 102 defines a lumen 103 (see FIG. 2) extending at least substantially entirely therethrough. Catheter sleeve 102 includes a proximal end portion 106 connected to and/or supporting a handle, hub or manifold 104, and a distal end portion 108 configured for passage of an elongated shaft 120 therethrough. Catheter sleeve 102 is fabricated utilizing suitable technology to provide catheter sleeve walls having predetermined flexibility characteristics that can allow precise intravascular navigation, pushability and trackability.

Thrombectomy catheter system 100 includes at least one electrode 110 disposed at and/or supported at distal end portion 108 of catheter sleeve 102. Desirably, a pair of electrodes 110a, 110b is provided at distal end portion 108 of catheter sleeve 102. Each electrode 110a, 110b is electrically connectable to a source of electrosurgical energy, such as, for example, an electrosurgical generator "G", via electrical conduits or wires 112 extending through lumen 103 of catheter sleeve 102 and through hub 104. Each electrode 110 may be electrically isolated and/or independent from one another.

As is described in greater detail below, electrodes 110a, 110b are preferably used to emulsify emboli or thrombi entrained in fluid flows (i.e., vessels) to prevent clogging of the channel or to ablate the embolus or thrombus to unclog the channel.

As seen in FIGS. 1-3, thrombectomy catheter system 100 further includes a shaft or guidewire 120 extendable through lumen 103 of catheter sleeve 102. Guidewire 120 includes a selectively deployable capture element 124 disposed proximate distal end 122 thereof. In one embodiment, capture element 124 is in the form of a filter or cage. Capture element 124 includes a first condition wherein capture element 124 is collapsed or retracted onto guidewire 120, and at least a second condition wherein capture element 124 is deployed or expanded to preferably span the entire lumen of the vessel or expand into apposition with the targeted vessel. Transformation of capture element 124 may be impelled by external mechanical means, or by self-activating memory material provided within capture element 124. Such mechanical memory may be imparted to the material of capture element 124 by thermal treatment to achieve a spring temper in stainless steel, for example, or to set a shape memory in a susceptible metal alloy, such as a binary nickel-titanium (nitinol) alloy. Other suitable methods of deploying and retracting capture element 124 will be readily apparent to one having ordinary skill in the art and are incorporated into the present disclosure without departing from the scope and spirit of the present disclosure.

In one embodiment, in use, as will be described in greater detail below, guidewire 120 is inserted into the lumen of catheter sleeve 102, through hub 104, and slidably advanced therethrough until distal end 122 of guidewire 120 extends out through distal end portion of catheter sleeve 102 and capture element 124 is positioned at or near a desired location within the vessel.

In an embodiment, catheter system 100 may also be a fixed-wire system or a rapid exchange system.

Figure 4A:
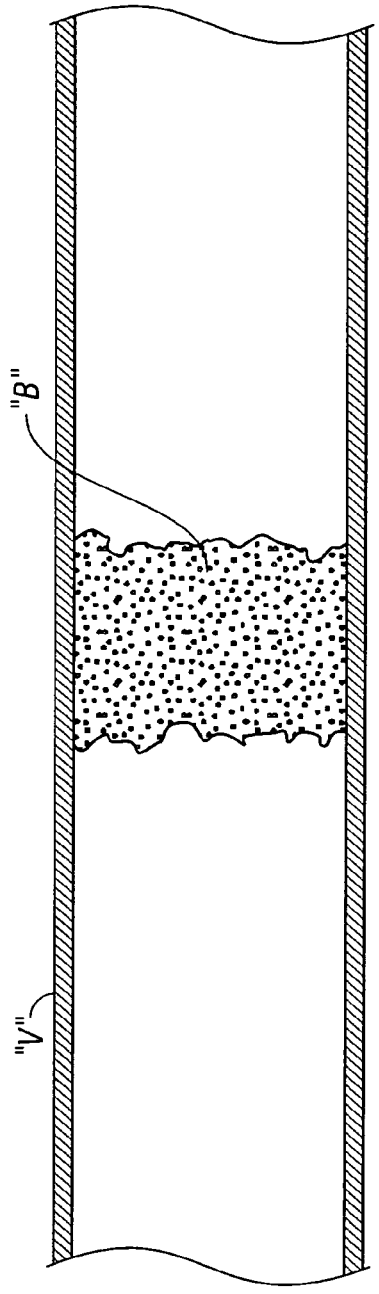
Figure 4B:
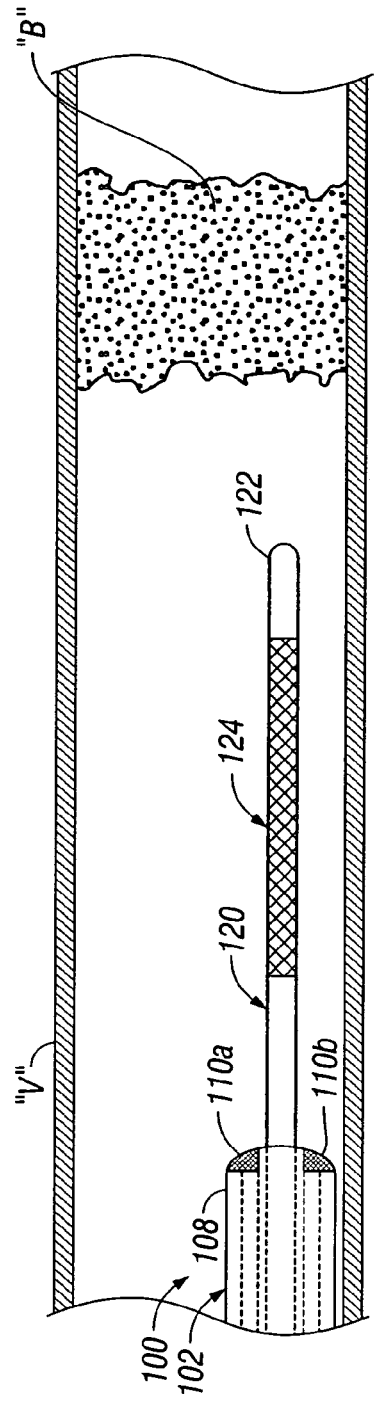
Figure 5:
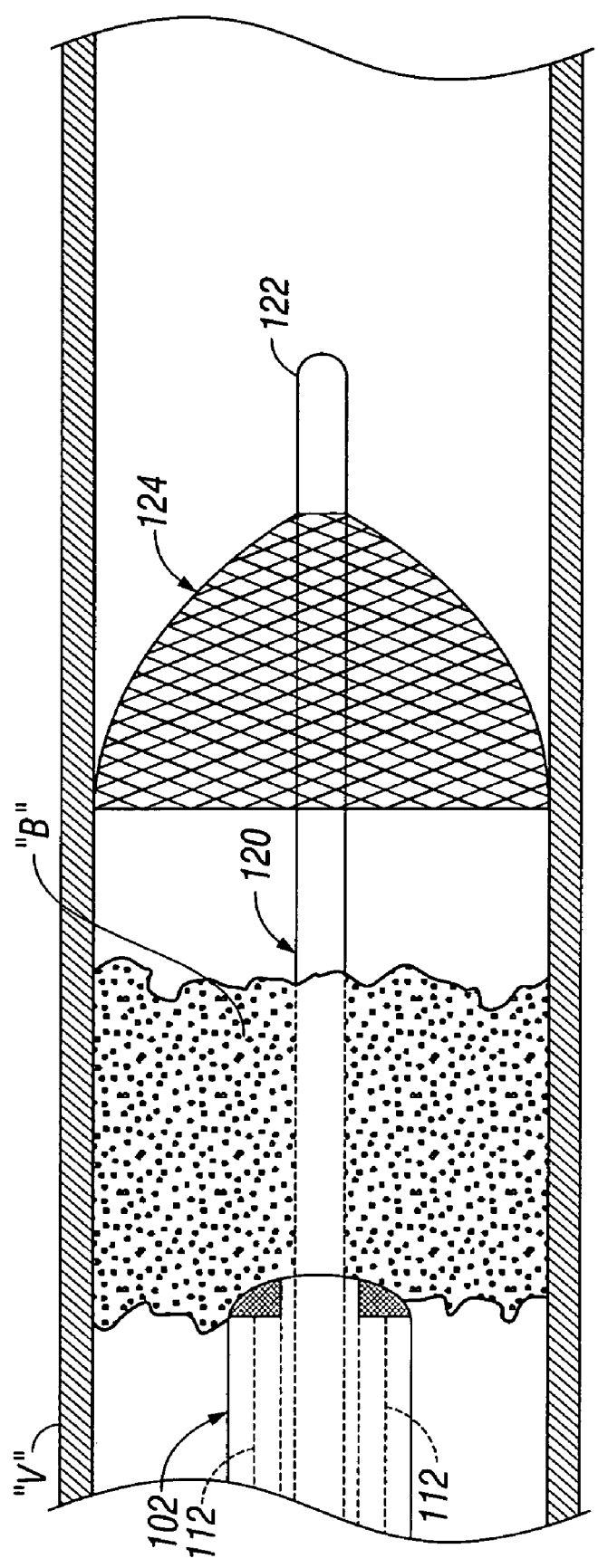
FIG. 5 is an enlarged schematic illustration of the thrombectomy catheter system of FIG. 4D, shown in a deployed condition within a blood vessel.

Turning now to FIGS. 4A-4D and 5, an exemplary method of using thrombectomy catheter system 100 is shown and described. FIG. 4A schematically depicts a vessel "V" containing a blockage or clot "B" (e.g., a thrombus, embolus, etc.) completely or substantially restricting blood flow therethrough. As seen in FIG. 4B, distal end portion 108 of catheter sleeve 102 is introduced into vessel "V" using any suitable technique.

A goal of the surgical procedure is to position capture element 124 of guidewire 120 distal of blockage "B", and to position distal end portion 108, and more particularly electrodes 110, against and/or within blockage "B". Accordingly, as seen in FIG. 4C, catheter sleeve 102 is advanced through vessel "V" until electrodes 110, disposed at distal end portion 108, are in close proximity to, are in contact with, or are positioned within, blockage "B". With continued reference to FIG. 4C, distal end 122 of guidewire 120 is advanced through blockage "B" until capture element 124 is disposed distal of blockage "B".

As seen in FIG. 4D, with capture element 124 of guidewire 120 located distally of blockage "B", capture element 124 is deployed to span the entire lumen of vessel "V". Once capture element 124 has been deployed, energy (e.g., thermal, RF, ultrasonic, electrical, plasma, etc.) is delivered to blockage "B" via electrodes 110. An effective amount of energy is delivered to electrodes 110 for an effective amount of time to ablate blockage "B". During and following ablation of blockage "B", any particularized thrombus and/or vapor, resulting from the ablation, is captured in capture element 124 of guidewire 120. In one embodiment, capture element 124 of guidewire 120 functions to trap and remove particles and/or debris that may flow distally or downstream through vessel "V" during the thrombectomy procedure.

As mentioned above, each electrode 110 may be electrically isolated and/or independent from one another. Accordingly, it is envisioned and within the scope of the present disclosure for each electrode 110 to be independently controlled by electrosurgical generator "G". During the procedure, it may be desirable to limit current flow to and between electrodes 110 when a low impedance path exists between electrodes 110 and a return or common electrode and/or when a high impedance path exists between electrodes 110 and a return or common electrode. Desirably, the energy delivered to electrodes 110 is in the range from about 20 kHz to about 20 MHz, and in the range of from about 5 volts to about 300 volts (RMS).

According to one embodiment and method, at least one or each electrode 110 may be configured to deliver plasma or the like. The surrounding blood or other fluid media may be the medium for generating the plasma.

In an embodiment, radio-opaque markers (not explicitly shown) may be provided along the length of catheter sleeve 102 and/or guidewire 120. In this manner, the position and location of the various elements of thrombectomy catheter system 100 (e.g., electrodes 110, capture element 124, etc.) may be monitored using conventional monitoring techniques, such as, for example, fluoroscopy and the like.

In one embodiment, thrombectomy catheter system 100 has an overall gauge that is less than about 0.060 inches. In this manner, thrombectomy catheter system 100 may enter and pass through present embolic protection devices that may be placed proximally of the blockage "B" during the thrombectomy procedure.

Figure 6:
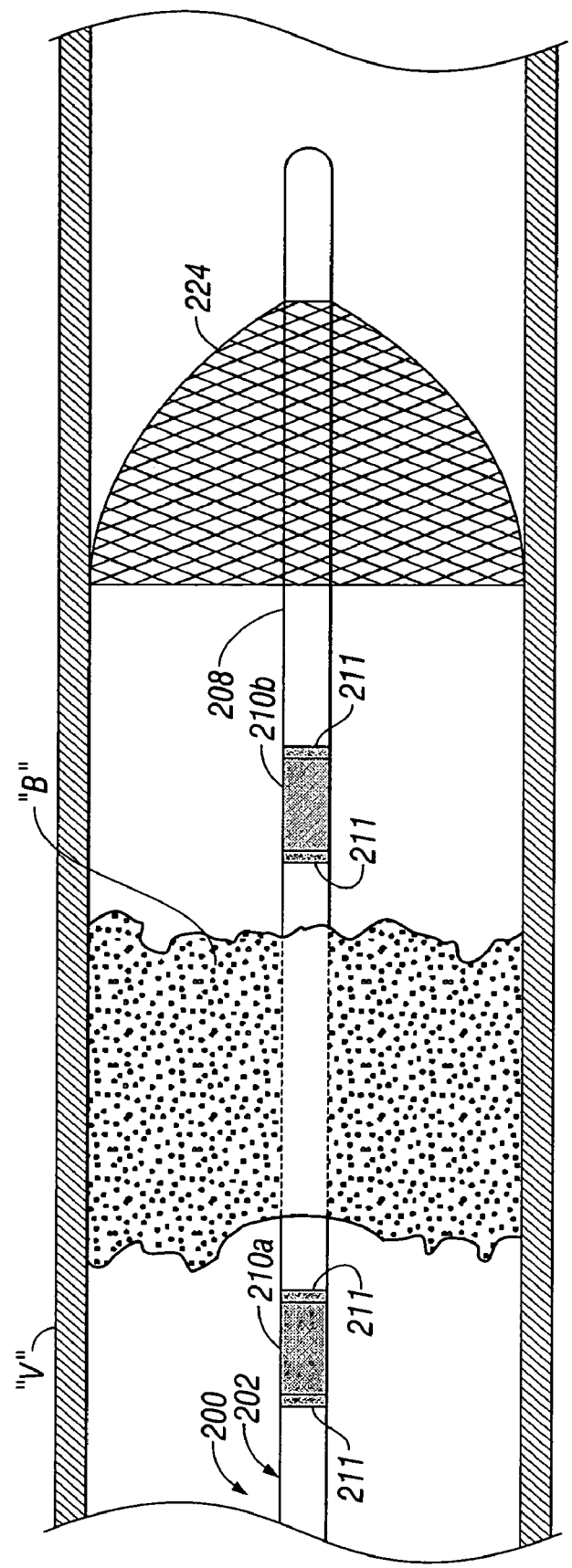
FIG. 6 is an enlarged schematic illustration of a thrombectomy catheter system, in accordance with another embodiment of the present disclosure, shown in a deployed condition within a blood vessel.

Turning now to FIG. 6, a thrombectomy catheter system, according to another embodiment of the present disclosure, is generally shown as 200. Thrombectomy catheter system 200 includes a catheter sleeve or body 202 having a distal end portion 208. Thrombectomy catheter system 200 further includes at least a pair of electrodes 210a, 210b disposed or supported thereon. Desirably, electrodes 210a, 210b are spaced an axial distance from one another and are preferably located proximate distal end portion 208. While only a pair of electrodes 210a, 210b are shown and described as being disposed on catheter sleeve 202, it is within the scope of the present disclosure for any suitable number of electrodes to be disposed along the length of catheter sleeve 202.

If more than a pair of electrodes 210a, 210b is provided, it may be desirable for the electrodes to be evenly spaced from one another. Additionally, each electrode 210a or 210b may be electrically isolated from one another. In an embodiment, radio-opaque markers 211 may be provided along the length of catheter sleeve 202, desirably on either side of each electrode 210a, 210b. Markers 211 provide the user, under fluoroscopic visualization, with the ability to identify when at least a distal-most electrode 210 is located distally of blockage "B". In one embodiment, each electrode 210a, 210b may substantially surround catheter sleeve 202.

As seen in FIG. 6, thrombectomy catheter system 200 further includes a capture element 224 disposed and/or supported on distal end portion 208 of catheter sleeve 202. Capture element 224 may be located distally of a distal-most electrode 210b. Capture element 224 is substantially similar to capture element 124 and will not be discussed in great detail hereinbelow.

Capture element 224 is in the form of a filter or cage. Capture element 224 includes a first condition wherein capture element 224 is collapsed or retracted onto catheter sleeve 202, and at least a second condition wherein capture element 224 is deployed or expanded to preferably span the entire lumen of the vessel or expands into apposition with the targeted vessel.

With continued reference to FIG. 6, an exemplary method of using thrombectomy catheter system 200, for performing a thrombectomy procedure, is shown and described. Once again, thrombectomy catheter system 200 is introduced into vessel "V" using any suitable technique.

A goal of the surgical procedure of FIG. 6 is to position capture element 224 through and distal of blockage "B", and to position catheter sleeve 202 through blockage "B" such that at least one electrode, e.g., distal-most electrode 210b, is located distal or downstream of blockage "B" and such that at least one electrode, e.g., proximal-most electrode 210a, is located proximal of or upstream of blockage "B". Accordingly, in use, catheter sleeve 202 is advanced through vessel "V" and through blockage "B" until distal-most electrode 210b is disposed distal of blockage "B" and capture element 224 is disposed distal of blockage "B".

As seen in FIG. 6, with capture element 224 of thrombectomy catheter system 200 located distally of blockage "B", capture element 224 is deployed to span the entire lumen of vessel "V". Once capture element 224 has been deployed, energy (e.g., thermal, RF, ultrasonic, electrical, etc.) is delivered to blockage "B" via electrodes 210a, 210b. An effective amount of energy is delivered to and between electrodes 210a, 210b, from electrosurgical generator "G", for an effective amount of time to ablate blockage "B". During the ablation process, the effective amount of energy is transmitted through blockage "B" between distal-most electrode 210b and proximal-most electrode 210a.

During and following ablation of blockage "B", any particularized thrombus and/or vapor, resulting from the ablation, is captured in capture element 224. In one embodiment, capture element 224 functions to trap and remove particles and/or debris that may flow distally or downstream through vessel "V" during the thrombectomy procedure.

While the devices and methods of the present disclosure have been directed to thrombectomy procedures and the like, it is within the present disclosure for the devices disclosed herein to be used in connection with other procedures equally as well, such as, for example, vascular stenosis, plaque removal, artherectomy and the like.

Various modifications may be made to the embodiments of the presently disclosed apparatus, devices and methods. Therefore, the above description should not be construed as limiting, but merely as exemplifications of embodiments. Those skilled in the art will envision other modifications within the scope and spirit of the present disclosure.

What is claimed is:

1. A catheter system for ablating a partial or a complete blockage of a corporal vessel, the catheter system comprising:
    a catheter sleeve including a capture element supported thereon at a location proximal to a distal end thereof,
    wherein the capture element includes a first condition wherein the capture element is retracted onto the catheter sleeve and a second condition wherein the capture element is capable of at least substantially spanning the entire lumen of the corporal vessel; and
    at least a pair of axially spaced apart electrodes supported on the catheter sleeve at a location proximal of the capture element, wherein each of the electrodes substantially surrounds the catheter sleeve.

2. The catheter system according to claim 1, wherein each electrode is isolated from one another.

3. The catheter system according to claim 2, wherein each electrode is electrically connectable to a source of electrosurgical energy.

4. The catheter system according to claim 2, further comprising a source of electrosurgical energy electrically connectable to each electrode of the catheter sleeve.

5. The catheter system according to claim 1, wherein the capture element forms a cage when in the second condition.

6. A catheter system for ablating a partial or a complete blockage of a corporal vessel, the catheter system comprising:
    a catheter sleeve having a distal end portion;
    a capture element disposed on the catheter sleeve at a location proximal to the distal end portion of the catheter sleeve, the capture element having a first condition wherein the capture element is retracted onto the catheter sleeve and a second condition wherein the capture element is capable of at least substantially spanning the entire lumen of the corporal vessel; and
    at least a pair of axially spaced apart electrodes supported on the catheter sleeve at a location proximal of the capture element, wherein each electrode is connectable to a source of electrosurgical energy, wherein the pair of axially spaced apart electrodes are separated from one another by a distance such that at least one electrode is disposed distal of the blockage and at least one electrode is disposed proximal of the blockage when the capture element is in the second condition.

7. The catheter system according to claim 6, wherein the catheter sleeve is flexible and enables pushability and trackability.

8. The catheter system according to claim 6, further comprising a source of electrosurgical energy electrically connectable to each electrode.

9. The catheter system according to claim 8, wherein the electrosurgical energy source delivers an effective amount of energy to the electrodes to ablate the blockage.

10. The catheter system according to claim 6, wherein the catheter sleeve has a gauge of about 0.060 inches.

11. The catheter system according to claim 6, further comprising at least one radio-opaque marker located in close proximity to each electrode.

12. A method of ablating a blockage in a corporal vessel comprising the steps of:
    introducing a catheter sleeve into the corporal vessel;
    advancing the catheter sleeve through the corporal vessel to the blockage,
    the catheter sleeve including a capture element supported thereon at a location proximal to a distal end thereof and at least a pair of axially spaced apart electrodes supported thereon, wherein each of the electrodes substantially surrounds the catheter sleeve;
    positioning the capture element downstream of the blockage;
    deploying the capture element to at least substantially span the lumen of the corporal vessel;
    positioning the catheter sleeve within the corporal vessel such that at least one electrode is positioned in close proximity to the blockage; and
    activating an electrosurgical energy source to energize the electrodes and ablate the blockage.

13. The method according to claim 12, further comprising the step of delivering an effective amount of energy for an effective amount of time to the blockage.

14. The method according to claim 12, wherein the capture element includes a first condition wherein the capture element is retracted onto the catheter sleeve and a second condition wherein the capture element at least substantially spans the entire lumen of the vessel.

15. The method according to claim 12, further comprising the step of advancing the catheter sleeve though the corporal vessel and through the blockage until the capture element and a distal-most electrode is positioned distal of the blockage.

16. The method according to claim 12, wherein each electrode of the catheter sleeve is electrically independent from one another.

17. The method according to claim 12, further comprising the step of positioning at least one marker proximate the electrodes to identify a location of at least one electrode relative to the blockage.

* * * * *